(12) United States Patent
Stad

(10) Patent No.: US 7,488,330 B2
(45) Date of Patent: Feb. 10, 2009

(54) MODULAR STATIC INTERVERTEBRAL TRIAL

(75) Inventor: Shawn Stad, Fall River, MA (US)

(73) Assignee: Depuy Spine, Inc., Raynham, MA (US)

( * ) Notice: Subject to any disclaimer, the term of this patent is extended or adjusted under 35 U.S.C. 154(b) by 93 days.

(21) Appl. No.: 11/339,883

(22) Filed: Jan. 26, 2006

(65) Prior Publication Data

US 2006/0167551 A1    Jul. 27, 2006

(51) Int. Cl.
*A61F 2/44* (2006.01)
(52) U.S. Cl. .................. 606/102; 623/17.11; 623/17.13; 623/17.15; 623/17.16; 606/246; 606/279; 606/86; 606/99
(58) Field of Classification Search .................. 606/61, 606/246, 279, 86, 99, 102; 623/17.11–17.16; 292/150, 163, 170, 175, 302, DIG. 37; 403/3, 403/4, 6, 9, 11, 12, 13, 24, 25, 49, 325
See application file for complete search history.

(56) References Cited

U.S. PATENT DOCUMENTS

| 6,102,950 | A  | * | 8/2000 | Vaccaro ................... 623/17.16 |
| 6,364,377 | B1 | * | 4/2002 | Ferguson .................... 292/175 |
| 7,118,142 | B2 | * | 10/2006 | Xu ............................. 292/139 |
| 7,235,104 | B2 | * | 6/2007 | Grinberg et al. .......... 623/17.14 |
| 2003/0167091 | A1 | * | 9/2003 | Scharf ...................... 623/17.11 |
| 2003/0187506 | A1 | * | 10/2003 | Ross et al. ............... 623/17.13 |
| 2004/0143332 | A1 |   | 7/2004 | Krueger |
| 2004/0167537 | A1 |   | 8/2004 | Errico |
| 2004/0236342 | A1 |   | 11/2004 | Ferree |
| 2005/0234555 | A1 |   | 10/2005 | Sutton |

* cited by examiner

*Primary Examiner*—Eduardo C Robert
*Assistant Examiner*—Andrew Yang
(74) *Attorney, Agent, or Firm*—Thomas M. DiMauro

(57) ABSTRACT

A modular, static intervertebral trial having interchangeable base members having different heights, and interchangeable endplates having different footprints and angles.

14 Claims, 3 Drawing Sheets

MODULAR STATIC INTERVERTEBRAL TRIAL

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

Prior to inserting the disc, however, the surgeon typically desires to insure that the properly sized implant has been identified for the particular patient. To this end, trial implants are commonly included within the instrument sets that allow the surgeon to temporarily insert the trial into the intervertebral disc space and assess whether the height and footprint of the trial would be appropriate for the actual implant to be inserted. Typically, a large number of trials are supplied in an instrument set, with each having a distinct height, lordotic angle and footprint.

US Published Patent Application No. 2004/0143332 ("Krueger"). discloses both a trial spacer and trial endplates. However, the trial endplates appear to be designed to engage to an inserter instrument that is then positioned within the disc space. See Krueger at [0154]. Therefore, it appears that Krueger teaches a dynamic trial, wherein the operator can vary the distance between the trial endplates by varying the force on the instrument.

US Published Patent Application No. 2004/0167537 ("Errico") also discloses a dynamic trial, wherein the operator can vary the distance between the trial endplates by varying the force on the instrument.

US Published Patent Application No. 2004/0236342 ("Ferree") discloses a modular articulating trial, wherein the articulating nature of the trial allows the relative angles of the trial endplates to vary with the orientation of the opposing natural vertebral endplates. See Ferree at [0097].

SUMMARY OF THE INVENTION

There are three primary parameters required when selecting the appropriate interbody device: footprint, lordotic angle, and height. Considering these parameters and their corresponding size range, there are a great number of possible implant configurations from which a surgeon can choose. While these sizing options enable the surgeon to better accommodate the patient population, selecting the appropriately sized implant becomes increasingly difficult.

The present invention solves this problem by providing a kit for building a modular static intervertebral trial having interchangeable base members having different heights, and interchangeable endplates having different footprints and angles. Thus, the present invention enables the surgeon to build a trial that accounts for each of these parameters to determine the proper size prior to inserting the implant.

The modular trial preferably has three components. The first two components are opposing endplates that are geometrically equivalent to the endplates of the candidate implants. In the kit, different endplate angles and footprints are provided. The third component is the base, which in the kit provides different heights corresponding to the heights of candidate implants.

Utilizing this kit can significantly reduce the number of trialing iterations required to determine the appropriately sized implant, as well as reduce the procedure time and, consequently, risk to the patient, and reduces the total number of components in the kit, more efficiently utilizing space within the constraints of the operating room.

DETAILED DESCRIPTION OF THE INVENTION

Figure 1:
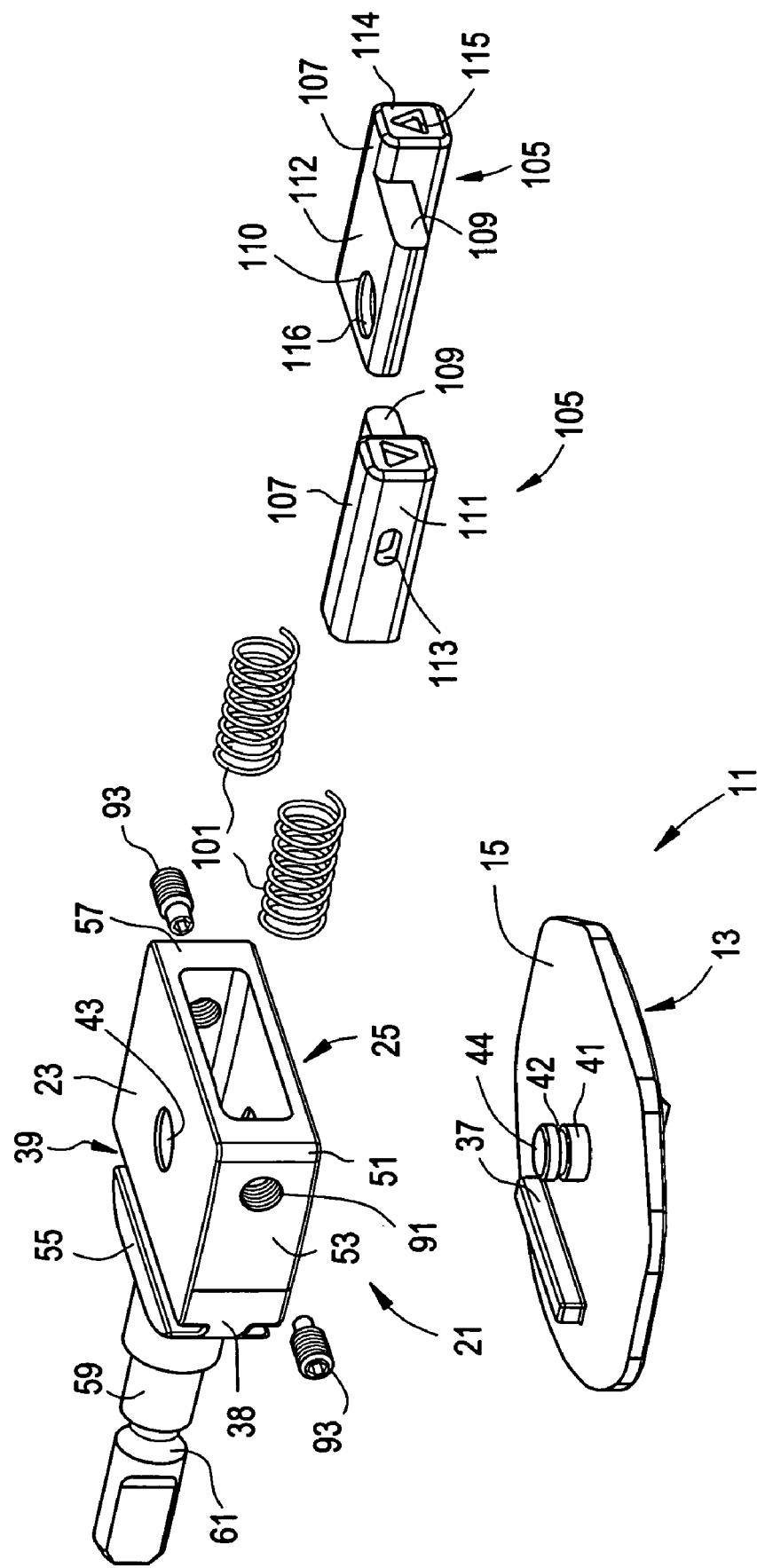
FIG. 1 is an exploded view of the modular trail of the present invention.

Now referring to FIG. 1, there is provided an exploded version of the modular static trial of the present invention. In particular, there is provided a modular intervertebral trial, comprising:

a) an upper trial vertebral endplate 1 comprising:
   i) an outer surface 3 adapted to mate with a first vertebral body,
   ii) an inner surface 5,
b) a lower trial vertebral endplate 11 comprising:
   i) an outer surface 13 adapted to mate with a second vertebral body, and
   ii) an inner surface 15
c) a base member 21 comprising:
   i) an upper surface 23 removably attached to the inner surface of the upper endplate, and
   ii) a lower surface 25 removably attached to the inner surface of the lower endplate.

In preferred embodiments, the outer surface of each endplate has a pair of parallel tracks 31 extending outwardly therefrom, wherein the tracks run in the anterior-posterior direction. These tracks are centered about the midline of the trial and are useful for keeping the endplate centered upon a rail of an inserter used to insert the trial into the disc space. The tracks also assist the surgeon in verifying the midline via fluoroscopy.

Preferably, the trial of the present invention contains radiographic features that aid in locating the device properly. Once the final trial location has been obtained, a midline marker can be placed relative to the trial position to act as a reference for the remainder of the procedure. Therefore, in some embodiments, each of the parallel tracks is provided with a notch 33, preferably extending into the track from the middle of the outer surface 35 thereof. In some embodiments, the notch extends into the track from a location slightly posterior of the middle of the outer surface 35 thereof. These notches serve as radiographic markers that preferably provide to the surgeon the precise location of the center of rotation.

In preferred embodiments, the inner surface of each endplate has a longitudinal rail 37 extending inwardly therefrom towards the base and in the medial-lateral direction. This rail is adapted to fit within a corresponding rail recess 39 upon an upper or lower surface of the base, and serves to prevent rotation of the endplate about the base.

In preferred embodiments, the inner surface of each endplate has a cylindrical post 41 extending inwardly therefrom towards the base substantially from the center of the endplate. Each post has an annular groove 42 disposed near the end 44 of the post. This post is adapted to be captured by a corresponding circular hole 43 upon an upper or lower surface of the base, and helps lock the endplate to the base.

In preferred embodiments, the base component of the modular trail comprises a housing 51 having upper 23 and lower 25 surfaces, lateral sidewalls 53, an anterior wall 55, and a posterior wall 57.

Each of the upper and lower walls has a circular hole 43 for reception of the endplate post. Each of the upper and lower walls also has a longitudinal rail recess 39 adapted for reception of the respective rails 37 of the corresponding endplates. These recesses are located near the anterior ends 38 of the upper and lower walls and run in the medial-lateral direction and The anterior wall 55 has a flange 59 extending anteriorly therefrom, wherein the flange has connection features 61 adapted for connection to a handle. In this case, connection feature 61 is a recess.

The posterior wall 57 of the base has a large window for reception of locking components.

In preferred embodiments, the locking components comprise a pair of springs 101 and a pair of locking buttons 105. The springs 101 are located in the anterior portion of the housing and run in the anterior-posterior direction. They provide a bias against the anterior ends of the locking buttons, and allow the locking buttons to be moved within the housing in the anterior-posterior direction.

Each locking button 105 comprises a longitudinal shaft 107 having a plate 109 extending medially from the medial wall of the shaft. The buttons 105 are located in the posterior portion of the housing and run in the anterior-posterior direction. They are held in place by the bias provided by their corresponding springs. The plate 109 of each button has a hole 110 on its outer surface 112 for capture of the endplate post of the respective endplate. Each of these holes 110 has a lip 116 on its anterior side. This lip is adapted to be received within annular groove 42 of the respective endplate post. The lateral wall 111 of the shaft has a recess 113 extending therethrough for capture by the locking nuts that have been received through the side walls 53. The posterior end face 114 of each locking button has a marker 115 that indicates the endplate corresponding to that button.

Preferably, each side wall 53 of the base has a posteriorly situated threaded hole 91 adapted for reception of a locking nut 93. This locking nut extends into the recesses 113 of the locking button to slidably mount the locking button in the housing in a position whereby the locking button hole 110 is aligned with the respective holes 43 in the upper and lower walls of the base, so that the endplate posts of the respective endplates may be locked in place.

Figure 2:
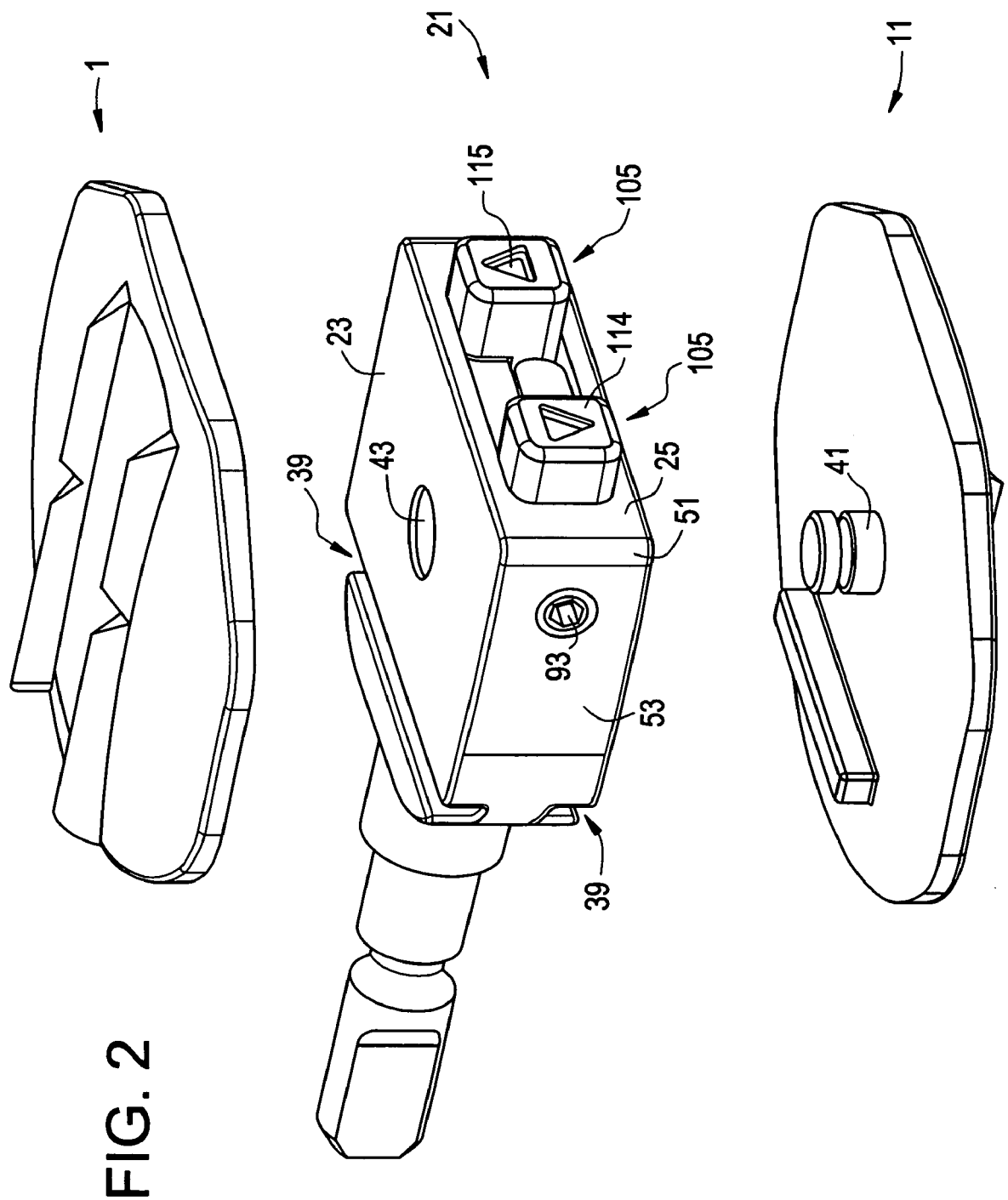
FIG. 2 is an exploded view of the assembled base and endplates of the present invention.
Figure 3:
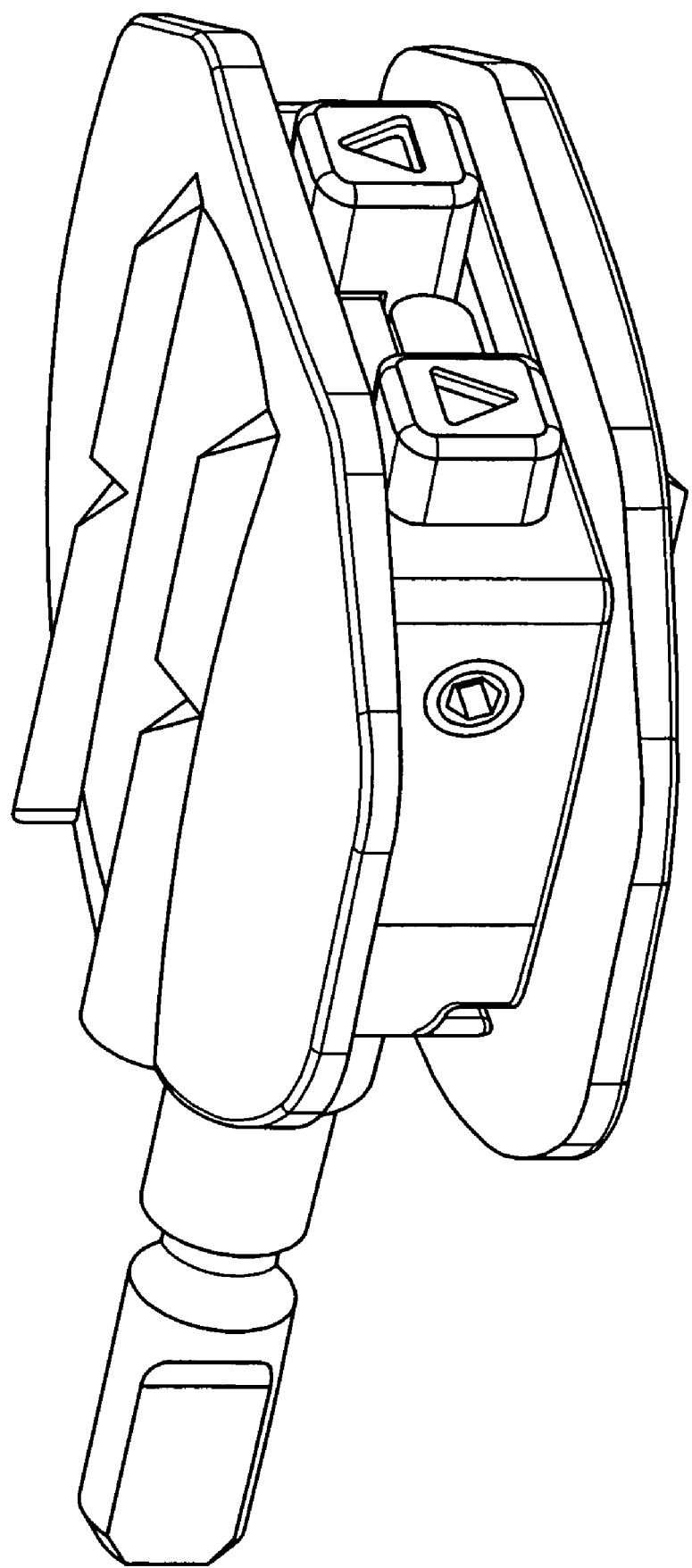
FIG. 3 is a perspective view of the modular trial of the present invention.

Now referring to FIG. 2, in use, the surgeon first selects candidate components, including a first base member 21, a first upper endplate 1 and a first lower endplate 11. The first base member is assembled so that the locking button hole is aligned with the respective holes in the upper and lower walls of the base, and locking nuts 93 help retain the locking buttons in the housing. The nuts are then tightened just enough to allow slidable mounting of the locking buttons within the housing. The surgeon then presses the endplate posts 41 of the selected endplates through the respective holes in the upper 23 and lower walls, and into the holes in the locking buttons, thereby locking the endplates to the base. The assembled modular trail is shown in FIG. 3. The surgeon then inserts the modular trial into the disc space and assesses its suitability.

If the surgeon decides to change one of the components (for example, the upper endplate) the surgeon then presses the corresponding locking button so that it moves in the anterior direction, thereby causing lip 116 to release from the annular grove of the post and releasing the endplate post and therefore the top endplate. The surgeon then inserts the endplate post of a second upper endplate through the hole in the upper wall, and into the hole in the respective locking button, thereby locking the second upper endplate to the base.

In some embodiments, the kit includes a plurality of base members, wherein the base members have different heights. Therefore, in accordance with the present invention, there is provided modular intervertebral trial, comprising:
  a) an upper trial vertebral endplate comprising:
    i) an outer surface adapted to mate with a first vertebral body,
    ii) an inner surface,
  b) a lower trial vertebral endplate comprising:
    i) an outer surface adapted to mate with a second vertebral body, and
    ii) an inner surface
  c) a plurality of base members having different heights, each base member comprising:
    i) an upper surface removably attached to the inner surface of the upper endplate, and
    ii) a lower surface removably attached to the inner surface of the lower endplate.

In some embodiments, the kit includes a plurality of trial vertebral endplates, wherein the endplates have different footprints. Therefore, in accordance with the present invention, there is provided modular intervertebral trial, comprising:
  a) a plurality of upper trial vertebral endplate having different footprints, each endplate comprising:
    i) an outer surface adapted to mate with a first vertebral body,
    ii) an inner surface,
  b) a lower trial vertebral endplate comprising:
    i) an outer surface adapted to mate with a second vertebral body, and
    ii) an inner surface
  c) a base member comprising:
    i) an upper surface removably attached to the inner surface of the upper endplate, and
    ii) a lower surface removably attached to the inner surface of the lower endplate.

In some embodiments, the kit includes a plurality of trial vertebral endplates, wherein the endplates have different angles. Therefore, in accordance with the present invention, there is provided modular intervertebral trial, comprising:
  a) a plurality of upper trial vertebral endplate having different angles, each endplate comprising:
    i) an outer surface adapted to mate with a first vertebral body,
    ii) an inner surface,
  b) a lower trial vertebral endplate comprising:
    i) an outer surface adapted to mate with a second vertebral body, and
    ii) an inner surface
  c) a base member comprising:
    i) an upper surface removably attached to the inner surface of the upper endplate, and
    ii) a lower surface removably attached to the inner surface of the lower endplate.

In preferred embodiments, each of the component is manufactured from a material that possesses the strength and high wear resistance desired for use as a motion disc trial component.

These components of the present invention may be made from any non-resorbable material appropriate for human surgical implantation, including but not limited to, surgically appropriate metals, and non-metallic materials, such as carbon fiber composites, polymers and ceramics.

In some embodiments, the base member is selected from the group consisting of polyethylene, PEEK, ceramic and metals. The endplate material is preferably selected from the group consisting of metal and composite (such as PEEK/carbon fiber).

If a metal is chosen as the material of construction for a component, then the metal is preferably selected from the group consisting of titanium, titanium alloys (such as Ti-6A1-4V), chrome alloys (such as CrCo or Cr—Co—Mo) and stainless steels.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; and mixtures thereof. Other suitable polymers may include RADEL and DELRIN$^R$.

If a ceramic is chosen as the material of construction for a component, then the ceramic is preferably selected from the group consisting of alumina, zirconia and mixtures thereof. It is preferred to select an alumina-zirconia ceramic, such as BIOLOX delta™, available from CeramTec of Plochingen, Germany.

I claim:

1. A modular static intervertebral trial, comprising:
   a) an upper trial vertebral endplate comprising:
      i) an outer surface adapted to mate with a first vertebral body,
      ii) an inner surface,
   b) a lower trial vertebral endplate comprising:
      i) an outer surface adapted to mate with a second vertebral body, and
      ii) an inner surface
   c) a base member comprising:
      i) an upper surface removably attached to the inner surface of the upper endplate, and
      ii) a lower surface removably attached to the inner surface of the lower endplate,
   wherein the base member comprises a housing having upper and lower surfaces, lateral sidewalls, an anterior wall, and a posterior wall, and
   wherein the anterior wall of the base member has a flange extending anteriorly therefrom, wherein the flange has a connection feature adapted for connection to a handle,
   wherein the housing houses locking components comprising an anterior pair of springs and a posterior pair of locking buttons, wherein each spring is positioned to bias its respective locking button.

2. The trial of claim 1 wherein the outer surface of the each endplate has a pair of parallel tracks extending therefrom.

3. The trial of claim 2 wherein at least one of the tracks has a notch therein.

4. The trial of claim 1 wherein the inner surface of each endplate has a post extending therefrom, the upper and lower surfaces of the base member each have a hole therein, and each post extends through the respective hole in the upper and lower surfaces of the base member.

5. The trial of claim 1 wherein the inner surface of each endplate has a longitudinal rail extending inwardly therefrom towards the base member, the upper and lower surfaces of the base member each has a longitudinal recess therein, and each longitudinal rail is received in the corresponding longitudinal recess.

6. The trial of claim 1 wherein the posterior wall of the base has a window for reception of locking components.

7. The trial of claim 1 wherein each locking button comprises a longitudinal shaft having a medial wall and a plate extending medially from the medial wall.

8. The trial of claim 7 wherein each plate of each button has an outer surface having a hole therein for capture of an endplate post of the respective endplate.

9. The trial of claim 8 where each hole has an anterior side having a lip thereon.

10. The trial of claim 9 wherein each endplate has a post extending from the inner surface thereof, wherein each post has an annular groove therein, and each lip is received within the annular groove of the respective endplate post.

11. The trial of claim 7 wherein the longitudinal shaft has a lateral wall having a recess extending therein.

12. The trial of claim 11 wherein a threaded locking nut is threadably received in a threaded hole of a lateral wall of a housing.

13. The trial of claim 1 wherein each locking button has a posterior end face having a marker thereon to indicate the endplate corresponding to the respective button.

14. The trial of claim 1 wherein the connection feature is a recess.

* * * * *